United States Patent
Lee et al.

(10) Patent No.: US 12,043,594 B2
(45) Date of Patent: Jul. 23, 2024

(54) BIPHENYL DERIVATIVE COMPOUND AND USE THEREOF

(71) Applicant: EWHA UNIVERSITY—INDUSTRY COLLABORATION FOUNDATION, Seoul (KR)

(72) Inventors: Kong Joo Lee, Seoul (KR); Hee-Yoon Lee, Daejeon (KR); Je Jin Lee, Seoul (KR); Hongsoo Lee, Daejeon (KR); Ji-wan Seo, Daegu (KR); Hwang Suk Kim, Suwon-si (KR); Bo-kyung Kim, Incheon (KR); Ji Soo Shin, Seoul (KR)

(73) Assignee: EWHA UNIVERSITY—INDUSTRY COLLABORATION FOUNDATION, Seoul (KR)

( * ) Notice: Subject to any disclaimer, the term of this patent is extended or adjusted under 35 U.S.C. 154(b) by 799 days.

(21) Appl. No.: 17/059,762

(22) PCT Filed: May 30, 2019

(86) PCT No.: PCT/KR2019/006518
§ 371 (c)(1),
(2) Date: Nov. 30, 2020

(87) PCT Pub. No.: WO2019/231261
PCT Pub. Date: Dec. 5, 2019

(65) Prior Publication Data
US 2021/0206706 A1    Jul. 8, 2021

(30) Foreign Application Priority Data

May 30, 2018 (KR) .................. 10-2018-0062144

(51) Int. Cl.
| | | |
|---|---|---|
| *C07C 43/23* | (2006.01) | |
| *A23L 33/00* | (2016.01) | |
| *A23L 33/10* | (2016.01) | |
| *A61K 9/00* | (2006.01) | |
| *A61K 31/09* | (2006.01) | |
| *A61K 31/12* | (2006.01) | |
| *A61K 31/337* | (2006.01) | |
| *A61P 35/00* | (2006.01) | |
| *C07C 49/175* | (2006.01) | |

(52) U.S. Cl.
CPC .............. *C07C 43/23* (2013.01); *A23L 33/10* (2016.08); *A23L 33/40* (2016.08); *A61K 9/0056* (2013.01); *A61K 31/09* (2013.01); *A61K 31/12* (2013.01); *A61K 31/337* (2013.01); *A61P 35/00* (2018.01); *C07C 49/175* (2013.01); *A23V 2002/00* (2013.01)

(58) Field of Classification Search
CPC .................................................. C07C 43/23
See application file for complete search history.

(56) References Cited

U.S. PATENT DOCUMENTS
2006/0270686 A1    11/2006 Kelly

FOREIGN PATENT DOCUMENTS
WO         9936391       7/1999
WO    2008038955 A1     4/2008

OTHER PUBLICATIONS

Registry No. 622408-06-4 (Dec. 1, 2003, STN).*
Registry No. 622408-05-3 (Dec. 1, 2003, STN).*
Registry No. 779341-15-0 (Nov. 12, 2004, STN).*
Registry No. 779341-28-5 (Nov. 12, 2004, STN).*
Wetzel, et al. Journal of Medicinal Chemistry 47 (2012) 1-17.*
Lala, et al. Cancer and Metastasis Reviews (1998), 17(1), 91-106.*
Golub, et al. Science 286, 531 (1999).*
Cancer [online], [retrieved on Aug. 11, 2023]. Retrieved from the internet, URL https://medlineplus.gov/cancer.html#>.*
International Preliminary Report on Patentability, International Patent Application PCT/KR2019/006518, dated Dec. 1, 2020.
International Search Report (Translation), International Patent Application PCT/KR2019/006518, dated Sep. 6, 2019.
Written Opinion (Translation), International Patent Application PCT/KR2019/006518, dated Sep. 6, 2019.
T.J. Korn, "Cobalt(II)-Catalyzed Cross-Coupling of Polyfunctional Aryl Copper Reagents with Aryl Bromides and Chlorides," Angew. Chemie Int'l Ed., 44, 2947-51 (2005).
M. Mor et al., "Cyclohexylcarbamic Acid 3¢- or 4¢-Substituted Biphenyl-3-yl Esters as Fatty Acid Amide Hydrolase Inhibitors: Synthesis, Quantitative Structure-Activity Relationships, and Molecular Modeling Studies," J. Med. Chem., 47, 4998-5008 (2004).
Brousmiche et al., "Supplementary Information for Photohydration and Photosolvolysis of Biphenyl Alkenes and Alcohols via Biphenyl Quinone Methide-type Intermediates and Diarylmethyl Carbocations," The Journal of the American Chemical Society, 125, 12961-12970 (2003).
Lin et al., "Activation of Antimetastatic Nm23-H1 Gene Expression by Estrogen and Its α-Receptor," Endocrinology, 143(2), 467-475 (2002).

* cited by examiner

*Primary Examiner* — Shawquia Jackson
(74) *Attorney, Agent, or Firm* — McDonnell Boehnen Hulbert & Berghoff LLP

(57) ABSTRACT

The present disclosure provides a novel biphenyl derivative compound, an optical isomer thereof or a pharmaceutically acceptable salt thereof. The biphenyl derivative compound, optical isomer thereof or pharmaceutically acceptable salt thereof according to the present disclosure may induce cancer cell death by damaging mitochondria and inducing ATP depletion in cells which are in a nutrient-starved state such as a glucose-starved state, which is the normal environment of cancer cells. In addition, it is an Nm23-H1/NDPK activity-increasing substance that may suppress cancer metastasis and growth. Thus, it exhibits excellent effects not only on the prevention, alleviation and treatment of cancer, but also on the suppression of cancer metastasis.

12 Claims, 5 Drawing Sheets

BIPHENYL DERIVATIVE COMPOUND AND USE THEREOF

CROSS-REFERENCE TO RELATED APPLICATIONS

This application is a U.S. National Stage entry of International Patent Application no. PCT/KR2019/006518, filed May 30, 2019, which claims the benefit of priority of Korean Patent Application no. 10-2018-0062144, filed May 30, 2018.

TECHNICAL FIELD

The present disclosure relates to a novel biphenyl derivative compound and the use thereof, and more particularly to a novel biphenyl derivative compound, a pharmaceutical composition for treating or preventing cancer containing the novel biphenyl derivative compound, an optical isomer thereof or a pharmaceutically acceptable salt thereof, a method for treating or preventing cancer comprising a step of administering the pharmaceutical composition, a pharmaceutical composition for suppressing cancer metastasis containing the novel biphenyl derivative compound, an optical isomer thereof or a pharmaceutically acceptable salt thereof, a method for suppressing cancer metastasis comprising a step of administering the pharmaceutical composition, a food composition for preventing or alleviating cancer containing the novel biphenyl derivative compound, an optical isomer thereof or a pharmaceutically acceptable salt thereof, and the use of the biphenyl derivative compound, an optical isomer thereof or a pharmaceutically acceptable salt thereof in the manufacture of a medicament for treating cancer.

BACKGROUND ART

Solid cancer cells proliferate along blood vessels, unlike normal cells or neurons. In particular, the solid cancer center has the property of proliferating even away from blood vessels. That is, when solid cancer cells are away from blood vessels, the cells are placed in microenvironmental conditions in which the supply of glucose or oxygen is not smooth. Under such stress condition, normal cells or neurons do not proliferate, but in the case of solid cancer cells, strong cell defense signaling pathways that enhance cell survival are activated by oncogenes that are expressed specifically in cancer cells. Metabolic changes of cancer cells by oncogenes such as c-Myc and KRAS cause specific metabolic mutations in cancer cells so that the cancer cells can adapt to changes in various tumor microenvironments such as hypoxia and nutrient starvation. Thus, targeting these metabolic changes has the advantage of inducing cancer cell-specific cell death. In addition, regarding the survival of cancer cells, particularly, solid cancer cells, it is important to kill cancer cells by overcoming stress resistance in cells placed in conditions where glucose supply is not smooth. Targeting mitochondrial mechanism in this process may be considered.

Meanwhile, tumor (cancer) metastasis is one of the most important factors determining the prognosis of cancer patients and is a major cause of cancer-related death. Although many efforts have been made to enable the survival of patients through cancer therapies, including surgery, radiotherapy and chemotherapy, efforts are still being made to increase the survival of cancer patients. The field of cancer metastasis research is one of the last strategies to overcome cancer, and research on cancer metastasis suppressors is essential in developing drugs for suppressing cancer metastasis.

Nm23 is a gene encoding a protein involved in the development and differentiation of normal tissue, and decreased expression of Nm23 in various metastatic cell lines has been reported. In general, Nm23 protein consisting of 150 to 180 amino acids contains a leucine zipper motif and has nucleoside diphosphate kinase (NDPK) activity. In particular, Nm23-H1 has been found to play an important role in cancer metastasis and other various cellular mechanisms, such as cell proliferation, embryonic development, differentiation, and tumor formation. Cancer metastasis occurs through a multi-step process in which cancer cells in a primary tumor tissue first invade blood vessels, and then move through the blood vessels, survive, and form new colonies at secondary sites. It has been found that Nm23, a nucleotide diphosphate kinase (NDPK), is a protein that converts NDPs (UDP, GDP, and CDP) to NTPs (UTP, GTP and CTP) using ATPs, and is an enzyme that regulates intracellular NTP levels. In addition, it has been found that overexpression of Nm23-H1 has a close relationship with decreased invasion of cancer cells. For example, WO1997-035024 discloses a method of treating cancer by administering a combination of enzymes including NDPK and a nucleoside analogue to cancer cells.

Based on this finding, studies have been conducted in the direction of increasing the expression of Nm23 or treating cells with cell-permeable Nm23-H1. Specifically, it was confirmed that treatment with MPA (medroxyprogesterone acetate) increased the expression level of Nm23-H1. This phenomenon is understood as a mechanism by which cancer metastasis is suppressed by MPA treatment. However, since treatment with MPA causes unexpected intracellular responses in addition to raising the level of Nm23-H1, MPA has not been used as a drug.

DISCLOSURE

Technical Problem

The present inventors have conducted extensive studies and made extensive efforts to develop agents capable of more effectively suppressing cancer development and metastasis, and as a result, have found that the use of newly developed biphenyl derivatives can prevent cancer development, treat developed cancer, and suppress metastasis of developed cancer, thereby completing the present disclosure.

Technical Solution

An object of the present disclosure is to provide a novel biphenyl derivative compound.

Another object of the present disclosure is to provide a pharmaceutical composition for treating or preventing cancer, the pharmaceutical composition containing the novel biphenyl derivative compound, an optical isomer thereof or a pharmaceutically acceptable salt thereof.

Still another object of the present disclosure is to provide a method for treating or preventing cancer, the method comprising a step of administering the pharmaceutical composition.

Yet another object of the present disclosure is to provide a pharmaceutical composition for suppressing cancer metastasis, the pharmaceutical composition containing the novel biphenyl derivative compound, an optical isomer thereof or a pharmaceutically acceptable salt thereof.

Still yet another object of the present disclosure is to provide a method for suppressing cancer metastasis, the method comprising a step of administering the pharmaceutical composition.

Further another object of the present disclosure is to provide a food composition for preventing or alleviating cancer containing the novel biphenyl derivative compound, an optical isomer thereof or a pharmaceutically acceptable salt thereof.

Still further another object of the present disclosure is to provide the use of the biphenyl derivative compound, an optical isomer thereof or a pharmaceutically acceptable salt thereof in the manufacture of a medicament for treating cancer.

Advantageous Effects

The novel biphenyl derivative compound of Formula 1, an optical isomer thereof or a pharmaceutically acceptable salt thereof according to the present disclosure can induce cancer cell death by damaging mitochondria and inducing ATP depletion in cells under a nutrient-starved state such as a glucose-starved state, which is supposed as the normal microenvironment of cancer cells. In addition, it is an Nm23-H1/NDPK activity-increasing substance that may suppress cancer metastasis and growth. Therefore, the composition according to the present disclosure exhibits excellent effects not only on the prevention, alleviation and treatment of cancer, but also on the suppression of cancer metastasis.

BEST MODE

Figure 1:
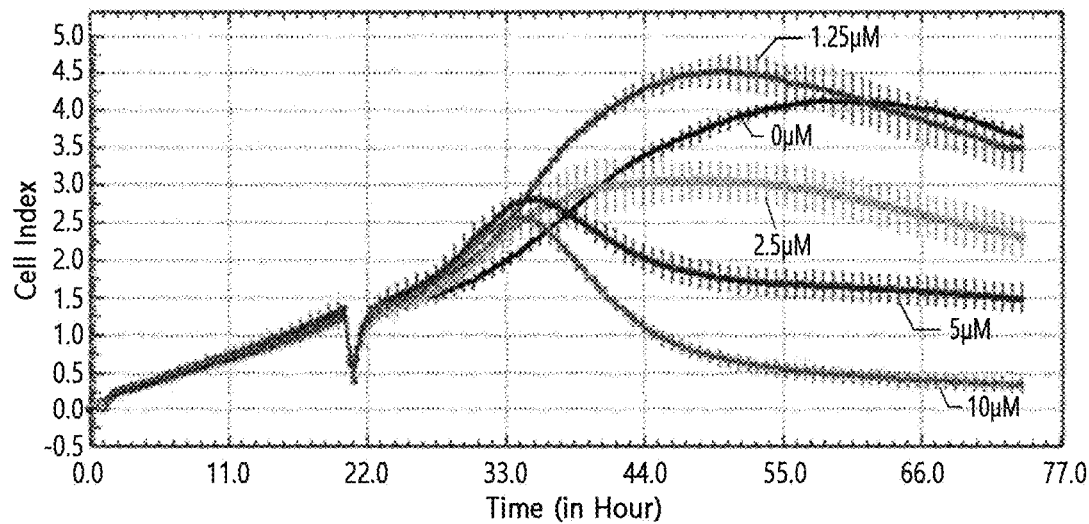
FIG. 1 shows the results of evaluating the cancer cell-killing effects of compounds according to the present disclosure by real-time cell proliferation assay under a glucose-starved condition.
Figure 1:
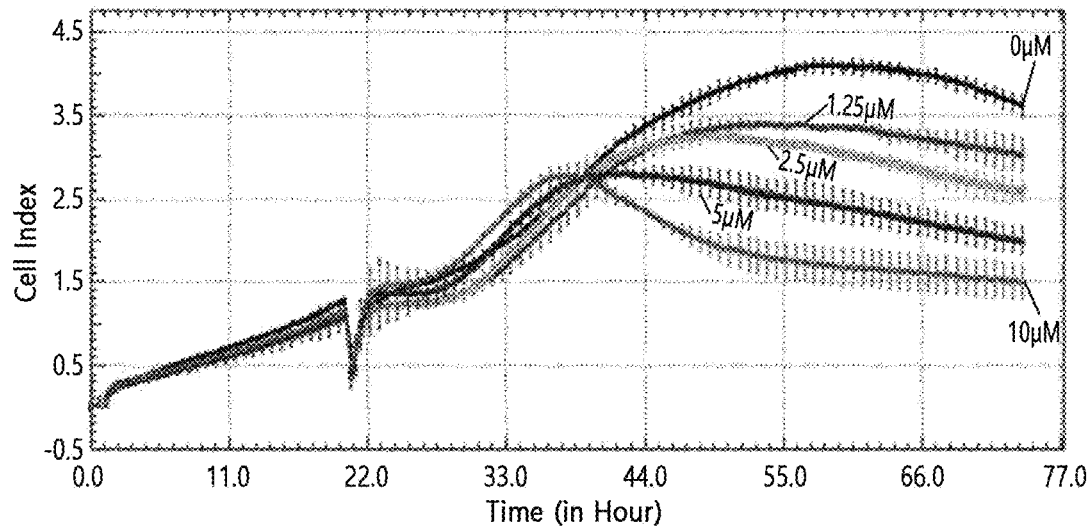

To achieve the above-described objects, one aspect of the present disclosure provides a novel biphenyl derivative compound of the following Formula 1, an optical isomer thereof or a pharmaceutically acceptable salt thereof:

[Formula 1]

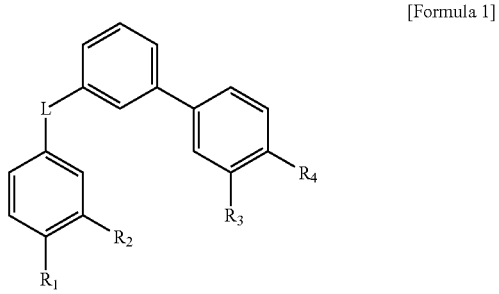

wherein
L is —(CH$_2$)—, —(C(=O))— or —(CHOH)—;
R$_1$ to R$_4$ are each independently hydrogen, hydroxy or a C$_1$ to C$_3$ alkoxy group; and
at least any one of R$_1$ to R$_4$ is hydroxy or a C$_1$ to C$_3$ alkoxy group.

Here, the C$_1$ to C$_3$ alkoxy group is any one selected from the group consisting of methoxy, ethoxy and propoxy groups.

Preferably, R$_1$ to R$_4$ are hydroxy or methoxy groups. More preferably, R$_1$ to R$_4$ are methoxy groups.

Preferably, L is —(CH$_2$)— or —(CHOH)—.

According to an embodiment of the present disclosure, the compound of Formula 1 may be any one selected from the group consisting of the following compounds:

| Example | Structure |
|---|---|
| 1 | 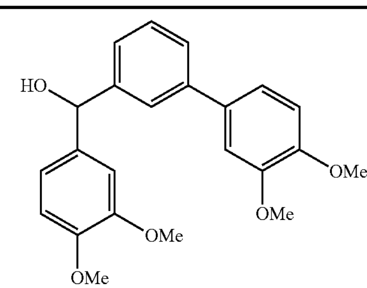 |

| Example | Structure |
|---|---|
| 1-1 | ![structure with HO, OMe groups] |
| 1-2 | ![structure with HO, OMe groups] |
| 2 | ![structure with OMe groups] |
| 3 | ![structure with O, OMe groups] |

The compound represented by Formula 1 according to the present disclosure may contain one or more asymmetric carbon atoms, and thus may exist as a racemate, a racemic mixture, a single enantiomer, a diastereomeric mixture, or each diastereomer.

For example, the compound of Example 1 is an optical isomer and may be separated in the form of Example 1-1 or Example 1-2.

This isomer may be separated by a conventional technique. For example, the compound represented by Formula 1 may be separated by resolution using column chromatography or HPLC. In addition, stereoisomers of the compound represented by Formula 1 may be stereo-specifically synthesized using optically pure starting materials with known configurations and/or reagents.

As used herein, the term "pharmaceutically acceptable salt" refers to salts which are commonly used in the pharmaceutical field. Examples of the salts include: inorganic ion salts formed with calcium, potassium, sodium, magnesium, etc.; inorganic acid salts formed with hydrochloric acid, nitric acid, phosphoric acid, bromic acid, iodic acid, perchloric acid, sulfuric acid, etc.; organic acid salts formed with acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc.; sulfonic acid salts formed with methanesulfonic acid, ethanesulfonic acid, benzenesulfonic acid, p-toluenesulfonic acid, naphthalenesulfonic acid, etc.; amino acid salts formed with glycine, arginine, lysine, etc.; and amine salts formed with trimethylamine, triethylamine, ammonia, pyridine, picoline, etc. However, the types of salts meant in the present disclosure are not limited to the above listed salts.

Another aspect of the present disclosure provides a method for producing the biphenyl derivative compound of Formula 1.

More specifically, the production of the compound of Formula 1 according to the present disclosure may be performed by a sequential or convergent synthetic route through the reaction route shown in Reaction Scheme 1 below.

[Reaction Scheme 1]

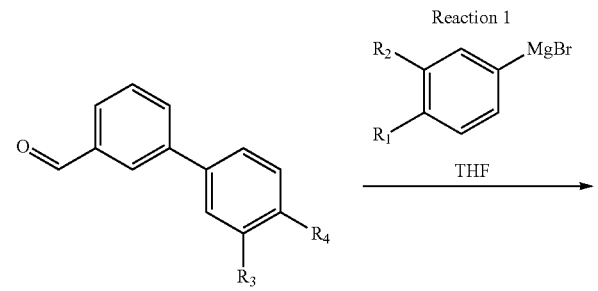

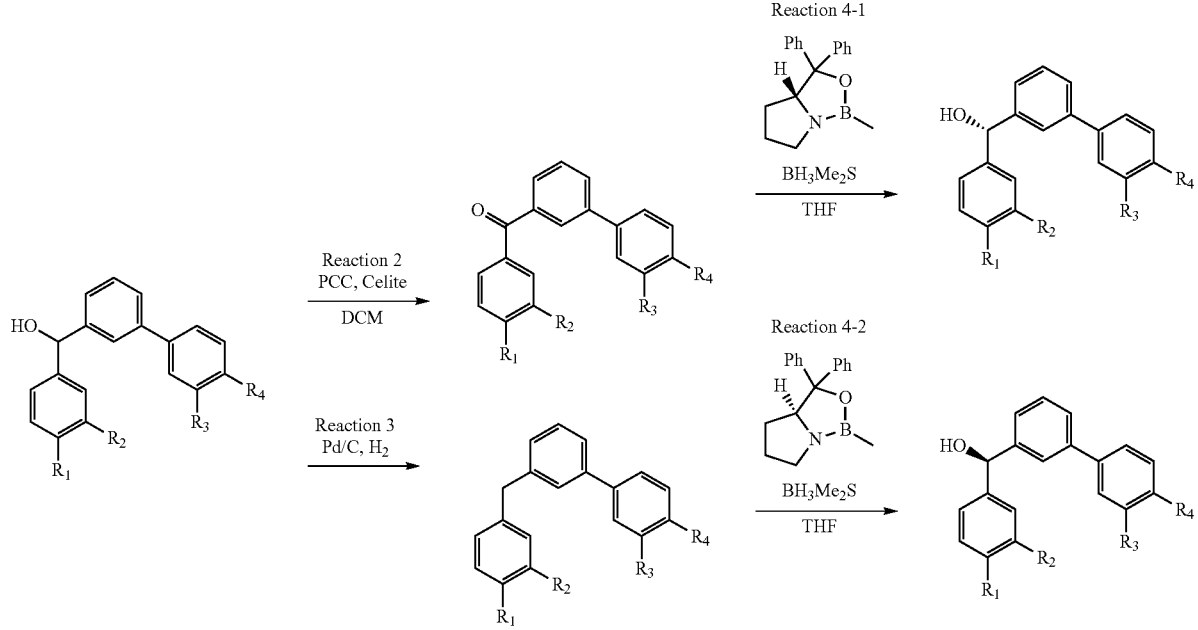

In Reaction 1 above, a [1,1'-biphenyl]-3-yl)(phenyl) methanol derivative may be produced by reacting a [1,1'-biphenyl]-3-carbaldehyde derivative with a phenyl magnesium bromide derivative. In Reaction 2, a ketone derivative may be synthesized by subjecting the [1,1'-biphenyl]-3-yl) (phenyl)methanol derivative to an oxidation reaction in the presence of PCC and Celite. In Reaction 3, a hydroxyl group may be removed from the [1,1'-biphenyl]-3-yl)(phenyl) methanol derivative through a reduction reaction in the presence of Pd/C and H2. In Reaction 4-1 or 4-2, the ketone derivative may be reacted with 2-methyl-CBS-oxazaborolidine and $BH_3Me_2S$ to produce each optical isomer.

According to one embodiment of the present disclosure, the biphenyl derivative compound of Formula 1 may be produced according to the sequence shown in the Reaction Scheme, but may also be produced by the method presented herein or a similar method. Thus, the synthetic route thereof is not limited to the route shown in the Reaction Scheme. The starting materials are commercially available or may be prepared by methods similar to the methods presented below.

Isolation and purification of the biphenyl derivative compound or intermediate produced by the above-described method may be effected by any suitable separation or purification procedure that is used in the pharmaceutical field, for example, filtration, extraction, crystallization, column chromatography, thin-layer chromatography, thick-layer chromatography, preparative low or high pressure liquid chromatography or a combination of these procedures.

Still another aspect of the present disclosure provides a pharmaceutical composition for treating or preventing cancer, the pharmaceutical composition containing the biphenyl derivative compound of Formula 1 or a pharmaceutically acceptable salt thereof as an active ingredient.

In the present disclosure, the cancer is not particularly limited as long as it may be treated or prevented by the biphenyl derivative compound of Formula 1 or pharmaceutically acceptable salt thereof provided according to the present disclosure. In one example, the cancer may be breast cancer, lung cancer, melanoma, prostate cancer, colorectal cancer, bladder cancer, bone cancer, blood cancer, thyroid cancer, parathyroid cancer, bone marrow cancer, rectal cancer, throat cancer, laryngeal cancer, esophageal cancer, pancreatic cancer, stomach cancer, tongue cancer, skin cancer, brain tumor, uterine cancer, head or neck cancer, gallbladder cancer, oral cancer, colon cancer, anal cancer, central nervous system tumor, liver cancer, colorectal cancer, or the like. In another example, the cancer may be breast cancer, lung cancer, colorectal cancer, skin cancer, or the like.

According to one embodiment of the present disclosure, the biphenyl derivative compound of Formula 1 or a pharmaceutically acceptable salt thereof is an Nm23-H1/NDPK activity-increasing substance that may suppress cancer metastasis and growth.

Accordingly, the biphenyl derivative compound of Formula 1 or a pharmaceutically acceptable salt thereof exhibits effects not only on the prevention or treatment of cancer, but also on the suppression of cancer metastasis.

According to one embodiment of the present disclosure, the biphenyl derivative compound of Formula 1, an optical isomer or a pharmaceutically acceptable salt thereof can induce cancer cell death by damaging mitochondria and inducing ATP depletion in cells under a nutrient-starved state such as a glucose-starved state, which is the normal microenvironment of cancer cells. In addition, it is an Nm23-H1/NDPK activity-increasing substance that can suppress cancer metastasis and growth.

Therefore, the biphenyl derivative compound of Formula 1, an optical isomer or a pharmaceutically acceptable salt thereof exhibits the effects of not only preventing or treating cancer, but also suppressing cancer metastasis.

As used herein, the term "treating" refers to any action of alleviating or beneficially changing symptoms of cancer by administering the biphenyl derivative compound or a pharmaceutically acceptable salt thereof.

As used herein, the term "preventing" refers to any action of suppressing or delaying cancer by administering the biphenyl derivative compound or a pharmaceutically acceptable salt thereof.

The pharmaceutical composition of the present disclosure may contain the biphenyl derivative compound or a pharmaceutically acceptable salt thereof in an amount of 0.001 to 80 wt %, specifically 0.001 to 70 wt %, more specifically 0.001 to 60 wt %, based on the total weight of the composition, but is not limited thereto.

For administration, the pharmaceutical composition of the present disclosure may further contain at least one pharmaceutically acceptable carrier in addition to the biphenyl derivative compound of Formula 1 or a pharmaceutically acceptable salt thereof. As the pharmaceutically acceptable carrier, it is possible to use saline, sterile water, Ringer's solution, buffered saline, dextrose solution, maltodextrin solution, glycerol, ethanol, or a mixture of two or more thereof. If necessary, the pharmaceutical composition may contain other conventional additives such as an antioxidant, a buffer and a bacteriostatic. In addition, the pharmaceutical composition may be formulated as an injectable formulation, such as an aqueous solution, a suspension or an emulsion, or a pill, capsule, granule or tablet formulation by further adding a diluent, a dispersant, a surfactant, a binder and a lubricant. Thus, the pharmaceutical composition of the present disclosure may be in the form of a patch, a liquid, a pill, a capsule, granules, a tablet, a suppository, etc. These formulations may be prepared by any conventional method that is used for formulation in the art or by a method disclosed in Remington's Pharmaceutical Science (the latest edition), Mack Publishing Company, Easton PA, and may be prepared in various forms depending on each disease or the components thereof.

The pharmaceutical composition of the present disclosure may be administered orally or parenterally (e.g., intravenously, subcutaneously, intraperitoneally or topically) according to a desired method, and the administration dose thereof may be in a wide range depending on the patient's body weight, age, sex, health condition and diet, the duration of administration, the mode of administration, excretion rate, and the severity of the disease. The compound of Formula 1 according to the present disclosure may be administered once or several times a day at a daily dose of about 1 to 1000 mg/kg, preferably 5 to 100 mg/kg.

The pharmaceutical composition of the present disclosure may further contain at least one active ingredient exhibiting a medicinal effect which is the same as or similar to that of the biphenyl derivative compound of Formula 1, an optical isomer thereof or a pharmaceutically acceptable salt thereof, in addition to the biphenyl derivative compound of Formula 1, an optical isomer thereof or a pharmaceutically acceptable salt thereof.

Even when the biphenyl derivative compound, an optical isomer thereof or a pharmaceutically acceptable salt thereof, which is provided according to the present disclosure, is used in combination with other known anticancer agent, the combination has a remarkable anticancer effect by exhibiting an excellent synergistic effect even at a low dose.

The known anticancer agent that may be used in this case is not particularly limited as long as it may exhibit anticancer activity of and a synergistic effect with the biphenyl derivative compound, an optical isomer thereof or a pharmaceutically acceptable salt thereof, which is provided according to the present disclosure. In one example, as the known anticancer agent, cisplatin, carboplatin, oxalliplatin, paclitaxel, docetaxel, vincristine, doxorubicin, daunorubicin, bleomycin, prednisone, methotrexate (MTX), 5-fluorouracil (5-FU), 6-mercaptopurine (6-MP), 6-thioguanine (6-TG), and the like may be used alone or in combination.

The present disclosure provides a pharmaceutical composition for suppressing cancer metastasis, the pharmaceutical composition containing, as an active ingredient, the biphenyl derivative compound of Formula 1 or a pharmaceutically acceptable salt thereof. The present disclosure also provides a method for suppressing cancer metastasis, the method comprising a step of administering the pharmaceutical composition to a subject that is at a risk of cancer metastasis or has metastasized cancer.

Here, the terms "biphenyl derivative compound", "pharmaceutically acceptable salt", "treating", "preventing" and "subject" are as defined above.

The composition according to the present disclosure exhibits an excellent effect of suppressing cancer metastasis by increasing Nm23-H1/NDPK activity.

The present disclosure also provides a method for treating or preventing cancer, the method comprising a step of administering the biphenyl derivative compound, an optical isomer thereof, a pharmaceutically acceptable salt thereof or the pharmaceutical composition for treating or preventing cancer to a subject that is a risk of developing cancer or has developed cancer.

Here, the terms "biphenyl derivative compound", "pharmaceutically acceptable salt", "treating" and "preventing" are as defined above.

As used herein, the term "subject" refers to all animals, including humans, rats, mice and domestic animals that have developed cancer or are at risk of developing cancer. In a specific example, the subject may be mammals including humans.

The pharmaceutical composition of the present disclosure is administered in a pharmaceutically effective amount. The term "pharmaceutically effective amount" refers to an amount sufficient to treat a disease at a reasonable benefit/risk ratio applicable to any medical treatment. The effective dose level of the pharmaceutical composition may be determined depending on factors including the subject's type, disease severity, age and sex, the activity of the drug, sensitivity to the drug, the duration of administration, the route of administration, excretion rate, the duration of treatment, and drugs used in combination with the composition, as well as other factors well known in the medical field. For example, the biphenyl derivative compound or a pharmaceutically acceptable salt thereof may be administered at a daily dose of 0.01 to 500 mg/kg, specifically 10 to 100 mg/kg, and the administration may be performed once or several times a day.

The treatment method according to the present disclosure also encompasses inhibiting or averting symptoms of a disease as well as addressing the disease itself, prior to the onset of symptoms by administering the compound of Formula 1. The prophylactic or therapeutic dose of a particular active ingredient in the management of a disease or condition may vary according to the nature and severity of the disease or condition and the route by which the active ingredient is administered. The dose and the dose frequency will also vary according to the age, body weight, and response of the individual patient. Suitable dosing regimens can be readily selected by those skilled in the art with due consideration of such factors. In addition, the treatment method according to the present disclosure may further comprise administering a therapeutically effective amount of an additional active agent helpful for the treatment of the disease together with the compound of Formula 1, in which the additional active agent may exhibit either a synergistic effect with the compound of Formula 1 or an assistant effect.

The present disclosure also provides a food composition for preventing or alleviating cancer, the food composition containing, as an active ingredient, the biphenyl derivative compound of Formula 1, an optical isomer thereof or a pharmaceutically acceptable salt thereof.

The food composition of the present disclosure may be used as a health functional food. The term "health functional food" refers to a food manufactured and processed using raw materials or ingredients that have functionality beneficial for the human body in compliance with the Health Functional Food Act No. 6727. The term "functionality" means that the intake of food is directed to controlling nutriments on the structure and function of the human body or achieving useful effects on health such as physiological effects.

The food composition of the present disclosure may contain conventional food additives. Unless otherwise specified, the suitability as food additives is determined by the specification and standard of the concerned item in compliance with General Provisions and General Test Methods of the Korean Food Additives Codex approved by the Korean Food and Drug Administration.

The food composition of the present disclosure may contain the compound of Formula 1 in an amount of 0.01 to 95 wt %, preferably 1 to 80 wt %, based on the total weight of the composition, for the purpose of preventing and/or alleviating cancer. In addition, the food composition may be manufactured and processed in the form of tablets, capsules, powders, granules, liquids, pills, beverages, etc. for the purpose of preventing and/or alleviating cancer.

The present disclosure also provides the use of the biphenyl derivative compound of Formula 1, an optical isomer thereof or a pharmaceutically acceptable salt thereof in the manufacture of a medicament for treating cancer.

The compound of Formula 1 for the manufacture of the medicament may be mixed with an acceptable adjuvant, diluent or carrier, etc., and may be combined with other active ingredients to form a combination formulation that exhibits a synergistic effect between the active ingredients.

The matters mentioned in the composition, use and treatment method of the present disclosure are equally applied unless they contradict each other.

MODE FOR INVENTION

Hereafter, examples of the disclosure will be described in detail so that the present disclosure can be easily carried out by those skilled in the art. However, the present disclosure may be embodied in various different forms and is not limited to the examples described herein.

In the following examples of the present disclosure, the reagents and solvents mentioned below are purchased from Sigma-Aldrich, TCI, unless otherwise specified, and HPLC was performed using a chiral IB column (Hex/iPA=80/20, 0.5 mL/min). As a silica gel for column chromatography, silica gel 60 (230-400 mesh ASTM) was used. $^1$H-NMR data were measured using Bruker Fourier Transform AV300 (300 MHz) spectrometers, Bruker Fourier Transform AV400 (400 MHz) spectrometers or Agilent Technologies DD2 (600 MHz).

Example 1. Synthesis of (3',4'-dimethoxy-[1,1'-biphenyl]-3-yl)(3,4-dimethoxyphenyl)methanol (HYL-NM-024)

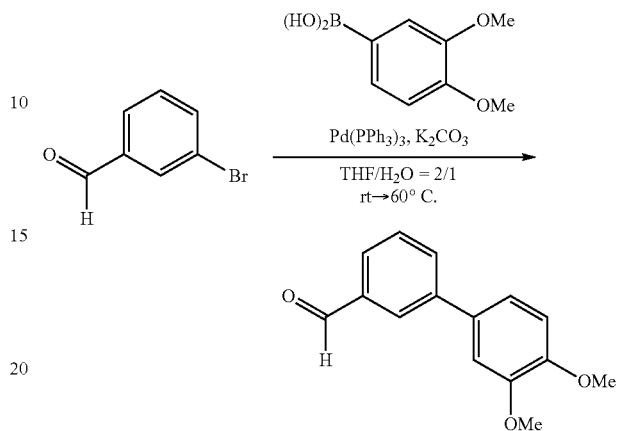

3-Bromobenzaldehyde (1.0 eq.) was added to a solution of boronic acid (2.0 eq.), $K_2CO_3$ (3.0 eq.) and Pd(PPh$_3$)$_4$ (0.01 eq.) in a 2:1 mixture of THF and $H_2O$. After stirring at 60° C. for 5 hours, the mixture was diluted with ethyl acetate, and then the reaction was terminated by adding aqueous ammonium chloride and water thereto. Then, the reaction mixture was extracted with ethyl acetate and then dried with MgSO$_4$. After filtration, the organic layer was concentrated and then purified on silica gel using column chromatography.

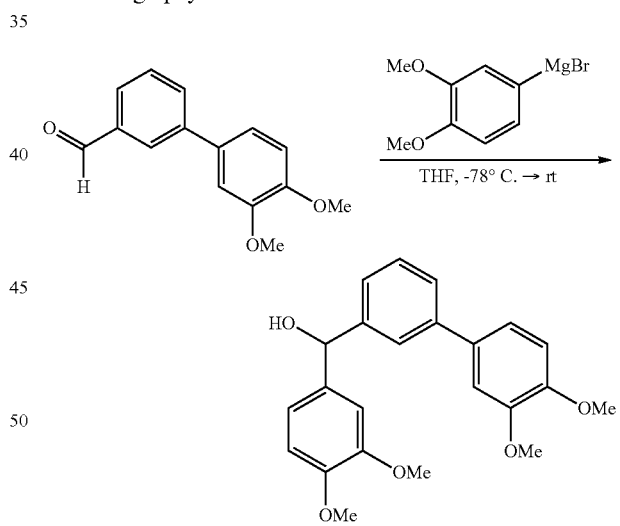

3',4'-dimethoxy-[1,1'-biphenyl]-3-carbaldehyde (1.0 eq.) was dissolved in tetrahydrofuran, and then 3,4-dimethoxyphenyl magnesium bromide (0.5M in THF) (3.0 eq.) was slowly added thereto at −78° C. The mixture was warmed to room temperature and then stirred for 30 minutes. After the reaction was terminated by adding aqueous ammonium chloride and distilled water thereto, the reaction mixture was dried with MgSO$_4$ and then concentrated. The resulting mixture was purified on silica gel using column chromatography.

$^1$H NMR (400 MHz, Chloroform-d) δ 7.57 (t, J=1.8 Hz, 1H), 7.45 (dt, J=7.7, 1.6 Hz, 1H), 7.37 (t, J=7.6 Hz, 1H), 7.31-7.24 (m, 1H), 7.14-7.04 (m, 2H), 6.95 (d, J=2.0 Hz, 1H), 6.93-6.87 (m, 2H), 6.81 (d, J=8.2 Hz, 1H), 5.84 (s, 1H), 3.91 (d, J=8.7 Hz, 6H), 3.84 (d, J=2.0 Hz, 6H).

Example 1-1. Synthesis of (S)-(3',4'-dimethoxy-[1,1'-biphenyl]-3-yl)(3,4-dimethoxyphenyl)methanol (HYL-NM-057)

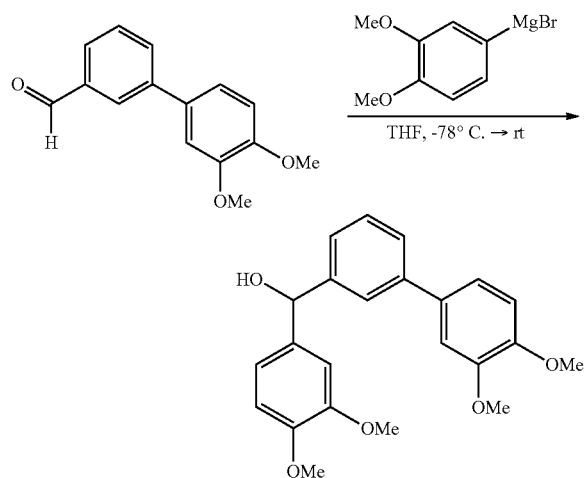

3',4'-dimethoxy-[1,1'-biphenyl]-3-carbaldehyde (1.0 eq.) was dissolved in tetrahydrofuran, and then 3,4-dimethoxyphenyl magnesium bromide (0.5M in THF) (3.0 eq.) was slowly added thereto at −78° C. The mixture was warmed to room temperature and then stirred for 30 minutes. After the reaction was terminated by adding aqueous ammonium chloride and distilled water thereto, the reaction mixture was dried with MgSO$_4$ and then concentrated. The resulting mixture was purified on silica gel using column chromatography.

$^1$H NMR (400 MHz, Chloroform-d) δ 7.57 (t, J=1.8 Hz, 1H), 7.45 (dt, J=7.7, 1.6 Hz, 1H), 7.37 (t, J=7.6 Hz, 1H), 7.31-7.24 (m, 1H), 7.14-7.04 (m, 2H), 6.95 (d, J=2.0 Hz, 1H), 6.93-6.87 (m, 2H), 6.81 (d, J=8.2 Hz, 1H), 5.84 (s, 1H), 3.91 (d, J=8.7 Hz, 6H), 3.84 (d, J=2.0 Hz, 6H).

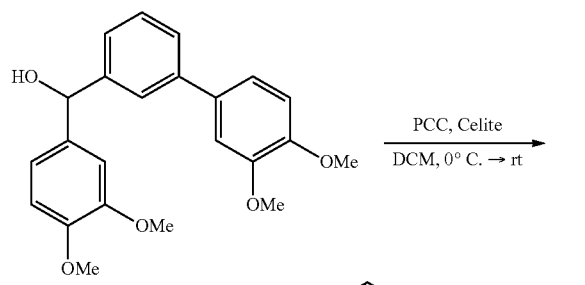

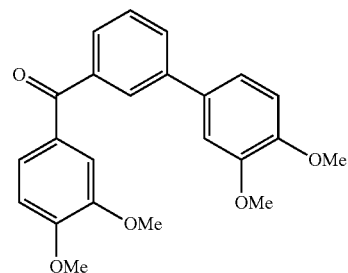 [SMILES: COc1ccc(C(=O)c2cccc(-c3ccc(OC)c(OC)c3)c2)cc1OC]

To the above-produced alcohol (1.0 eq.) in dichloromethane at 0° C., PCC (2.1 eq.) and celite (the same weight as PCC) were added. After the mixture was stirred until the starting material was completely consumed, the mixture was filtered through celite and then washed with ether. The collected organic mixture was concentrated and then purified on silica gel using column chromatography.

$^1$H NMR (400 MHz, Chloroform-d) δ 7.98-7.86 (m, 1H), 7.74 (dt, J=7.8, 1.4 Hz, 1H), 7.64 (d, J=7.8 Hz, 1H), 7.56-7.43 (m, 2H), 7.40 (dd, J=8.4, 2.0 Hz, 1H), 7.18-7.05 (m, 2H), 6.90 (dd, J=24.1, 8.3 Hz, 2H), 3.96-3.89 (m, 12H).

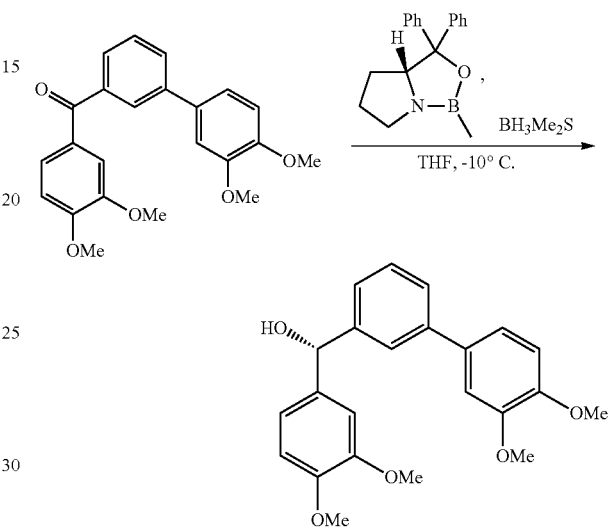

To a solution of ketone (1.0 eq.) in tetrahydrofuran at −10° C., (R)-2-methyl-CBS-oxazaborolidine (1.0 M in toluene) (1.02 eq.) was added. Then, BH$_3$Me$_2$S (3.0 eq.) was slowly added thereto dropwise. After 30 minutes, the reaction was terminated by adding 0.05 mL of methanol and 3 mL of distilled water thereto, and the organic mixture was extracted with ethyl acetate. The extract was dried with MgSO$_4$ and then concentrated. The resulting mixture was purified on silica gel using column chromatography.

$^1$H NMR (400 MHz, Chloroform-d) δ 7.57 (t, J=1.8 Hz, 1H), 7.44 (dt, J=7.7, 1.5 Hz, 1H), 7.37 (t, J=7.6 Hz, 1H), 7.32-7.22 (m, 1H), 7.16-7.04 (m, 2H), 6.98-6.86 (m, 3H), 6.80 (d, J=8.2 Hz, 1H), 5.83 (s, 1H), 3.90 (d, J=8.8 Hz, 6H), 3.83 (d, J=2.3 Hz, 6H).

Example 1-2. Synthesis of (R)-(3',4'-dimethoxy-[1,1'-biphenyl]-3-yl)(3,4-dimethoxyphenyl)methanol (HYL-NM-058)

The title enantiomer was synthesized in the same manner as HYL-NM-057.

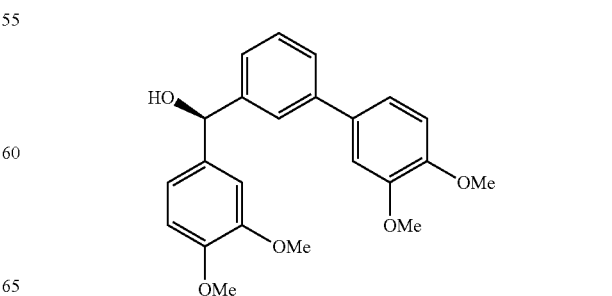

¹H NMR (400 MHz, Chloroform-d) δ 7.57 (t, J=1.8 Hz, 1H), 7.49-7.42 (m, 1H), 7.37 (t, J=7.6 Hz, 1H), 7.33-7.23 (m, 1H), 7.14-7.06 (m, 2H), 6.97-6.85 (m, 3H), 6.81 (d, J=8.2 Hz, 1H), 5.84 (s, 1H), 3.91 (d, J=8.7 Hz, 6H), 3.84 (d, J=1.8 Hz, 6H).

Example 2. 3'-(3,4-dimethoxybenzyl)-3,4-dimethoxy-1,1'-biphenyl (HYL-NM-025)

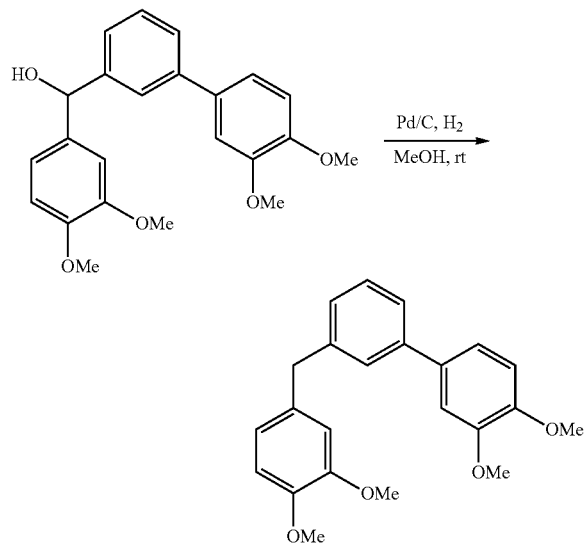

The compound (1.0 eq.) of Example 1 was dissolved in methanol, and then Pd/C (10 wt %) (0.1 eq.) was added thereto for 2 hours under a hydrogen atmosphere. After filtration through silica and celite, the collected organic mixture was concentrated and purified on silica gel using column chromatography.

¹H NMR (300 MHz, Chloroform-d) δ 7.44-7.28 (m, 3H), 7.09 (ddd, J=11.8, 5.4, 2.3 Hz, 3H), 6.91 (d, J=8.2 Hz, 1H), 6.83-6.71 (m, 3H), 3.98 (s, 2H), 3.91 (d, J=6.8 Hz, 6H), 3.83 (d, J=5.9 Hz, 6H).

Example 3. (3',4'-dimethoxy-[1,1'-biphenyl]-3-yl)(3,4-dimethoxyphenyl)methanone (HYL-NM-031)

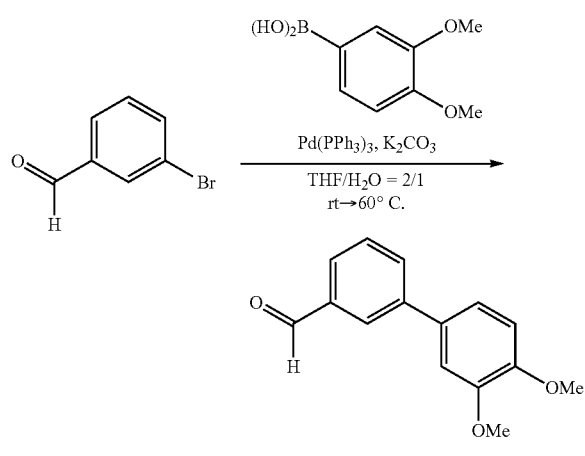

To a solution of boronic acid (2.0 eq.), K₂CO₃ (3.0 eq.) and Pd(PPh₃)₄ (0.01 eq.) in a 2:1 mixture of THF and H₂O, 3-bromobenzaldehyde (1.0 eq.) was added. After stirring at 60° C. for 5 hours, the mixture was diluted with ethyl acetate, and then the reaction was terminated by adding aqueous ammonium chloride and water thereto. Next, the reaction mixture was extracted with ethyl acetate and then dried with MgSO₄. After filtration, the organic layer was concentrated and then purified on silica gel using column chromatography.

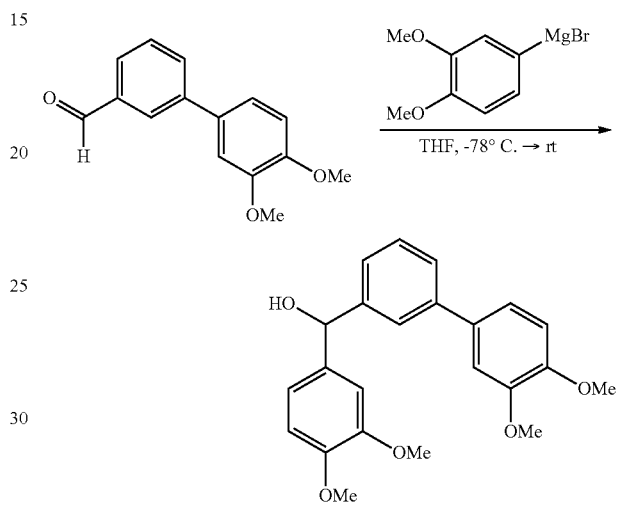

3',4'-dimethoxy-[1,1'-biphenyl]-3-carbaldehyde (1.0 eq.) was dissolved in tetrahydrofuran, and then 3,4-dimethoxyphenyl magnesium bromide (0.5 M in THF) (3.0 eq.) was slowly added thereto at −78° C. The mixture was warmed to room temperature and then stirred for 30 minutes. After the reaction was terminated by adding aqueous ammonium chloride and distilled water thereto, the reaction mixture was dried with MgSO₄ and then concentrated. The resulting mixture was purified on silica gel using column chromatography.

¹H NMR (400 MHz, Chloroform-d) δ 7.57 (t, J=1.8 Hz, 1H), 7.45 (dt, J=7.7, 1.6 Hz, 1H), 7.37 (t, J=7.6 Hz, 1H), 7.31-7.24 (m, 1H), 7.14-7.04 (m, 2H), 6.95 (d, J=2.0 Hz, 1H), 6.93-6.87 (m, 2H), 6.81 (d, J=8.2 Hz, 1H), 5.84 (s, 1H), 3.91 (d, J=8.7 Hz, 6H), 3.84 (d, J=2.0 Hz, 6H).

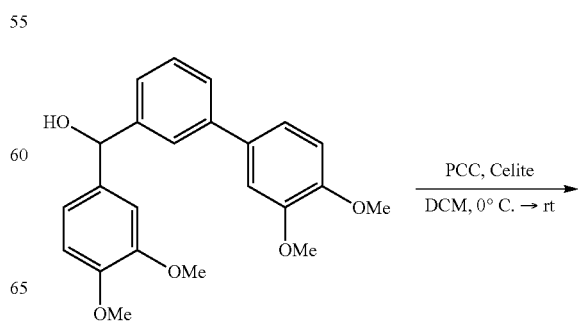

-continued

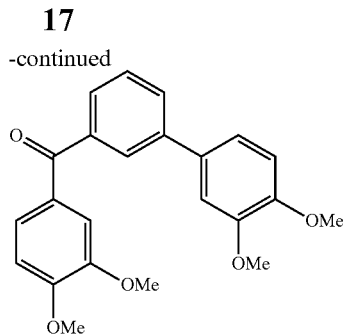

To the above-produced alcohol (1.0 eq.) in dichloromethane at 0° C., PCC (2.1 eq.) and celite (the same weight as PCC) were added. After the mixture was stirred until the starting material was completely consumed, the mixture was filtered through celite and then washed with ether. The collected organic mixture was concentrated and then purified on silica gel using column chromatography.

$^1$H NMR (400 MHz, Chloroform-d) δ 7.98-7.86 (m, 1H), 7.74 (dt, J=7.8, 1.4 Hz, 1H), 7.64 (d, J=7.8 Hz, 1H), 7.56-7.43 (m, 2H), 7.40 (dd, J=8.4, 2.0 Hz, 1H), 7.18-7.05 (m, 2H), 6.90 (dd, J=24.1, 8.3 Hz, 2H), 3.96-3.89 (m, 12H).

The structures of the compounds of the present disclosure, produced in Examples 1, 1-1, 1-2, 2 and 3, were identified and summarized in Table 1 below.

[Table 1]

| Example | Structure |
| --- | --- |
| 1 | 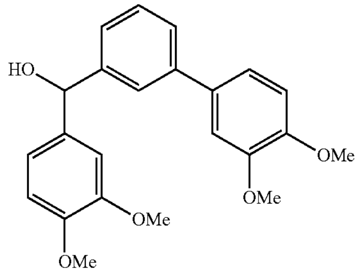 [SMILES: COc1ccc(-c2cccc(C(O)c3ccc(OC)c(OC)c3)c2)cc1OC] |
| 1-1 | 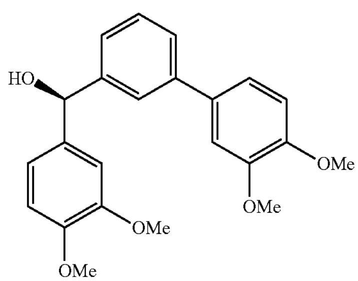 [SMILES: COc1ccc(-c2cccc([C@H](O)c3ccc(OC)c(OC)c3)c2)cc1OC] |
| 1-2 | 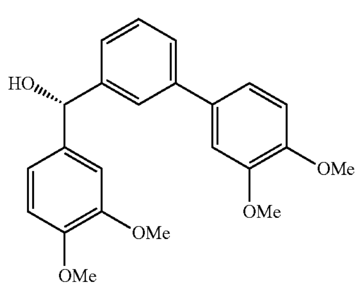 [SMILES: COc1ccc(-c2cccc([C@@H](O)c3ccc(OC)c(OC)c3)c2)cc1OC] |
| 2 | |
| 3 | |

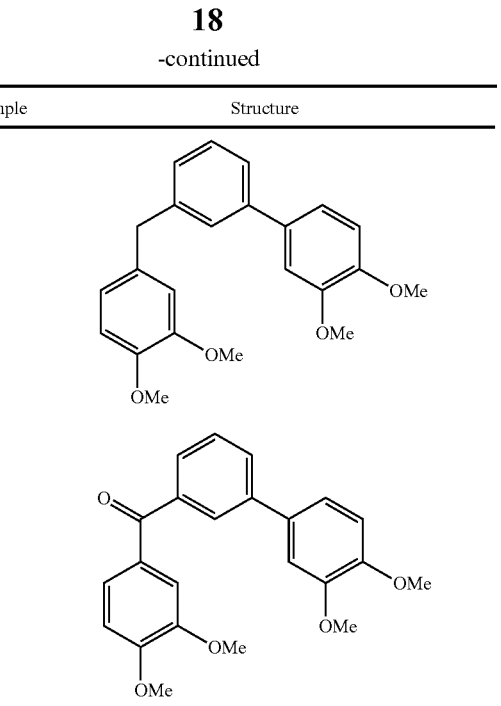

Example 4. Validation of Increased NDPK Activity

NDPK assay was performed by incubating 5 ng of recombinant Nm23-H1 with each of test compounds (Examples 1 to 3) in NDPK assay buffer (20 mM HEPES, 3 mM MgCl$_2$) at room temperature for 10 minutes, followed by reaction with 5 μM ADP for 1 minute.

The same effect was confirmed through cell-based NDPK assay, and the cell-based NDPK assay was performed as follows. 5,000K MDA-MB-231 cells were lysed with a protease inhibitor cocktail and an NDPK assay buffer, and the obtained cell lysate was centrifuged at 8,000 rpm at 4° C. for 10 minutes. 40 μL of the lysate was incubated with each test compound for 5 minutes, and then 50 μM UDP was added thereto, followed by reaction with NDPK. ATP consumption was assessed by an ATP determination kit (Molecular probe, USA).

The results are shown in Table 2 below.

TABLE 2

| Compound of Example | NDPK activity |
| --- | --- |
| 1 | 2.8 |
| 2 | 1.4 |
| 3 | 1.7 |

As shown above, it was confirmed that the compounds of the Examples exhibited an excellent effect of increasing NDPK activity (increasing Nm23-H1 activity).

Example 5. Evaluation of Cancer Cell Anti-Proliferative Effect Under Glucose-Starved Condition (Real-Time Cell Proliferation Assay)

The cancer anti-proliferative effects of the compounds of the present disclosure were evaluated by treating MDA-MB-231 cells with the compounds under a glucose-starved condition.

Cell proliferation and viability were measured in real time using xCELLigence RTCA SP (ACEA Bioscience). 50 μl of cell culture medium was added to an RTCA plate and a background was established. Then, MDA-MB-231 cells were seeded into the plate at a density of $7.5 \times 10^3$ cells/well, and an experiment was performed. At 24 hours, each of the compounds of the Examples (Example 1: B024; and Example 2: B025) was diluted in two types of EMEM-CM media with or without glucose, and the cells were treated with each of the dilutions. Cell proliferation was measured using xCELLigence RTCA at 15-minute intervals for a total of 72 hours.

The results are shown in FIG. 1.

As shown in FIG. 1, it was confirmed that treatment with the compounds according to the present disclosure significantly inhibited cancer cell proliferation under the glucose-starved condition. This indicates that the compounds according to the present invention have an excellent effect of cancer anti-proliferation under a glucose-starved condition, which is the generally known microenvironment of cancer cells.

Example 6. Evaluation of Mitochondrial Inhibitory Effect in Cancer Cells (Measurement of Oxygen Consumption Rate (OCR))

The oxygen consumption rate of MDA-MB231 cells was measured using an XFp Seahorse Bioscience Extracellular Flux Analyzer (Agilent). One day before analysis, MDA-MB231 cells were seeded into a Seahorse cell plate at a density of $2 \times 10^4$ cells/well, and the cells were cultured for 24 hours and then used in the experiment. Before analysis, cells for XF analysis were equilibrated at 37° C. for about 60 minutes in an assay medium (XF Base Medium, Seahorse Bioscience) containing 4 mM L-glutamine (Sigma-Aldrich) and 1 mM sodium pyruvate (Sigma-Aldrich) and adjusted to pH 7.4. During analysis, various concentrations (2.5, 5 and 10 μM) of the compound (Example 1), oligomycin (1 μM, ATP synthesis inhibitor), FCCP (0.5 μM, mitochondrial uncoupler) and rotenone/antimycin A (0.5 μM, mitochondrial ETC inhibitor) were sequentially injected.

Figure 2:
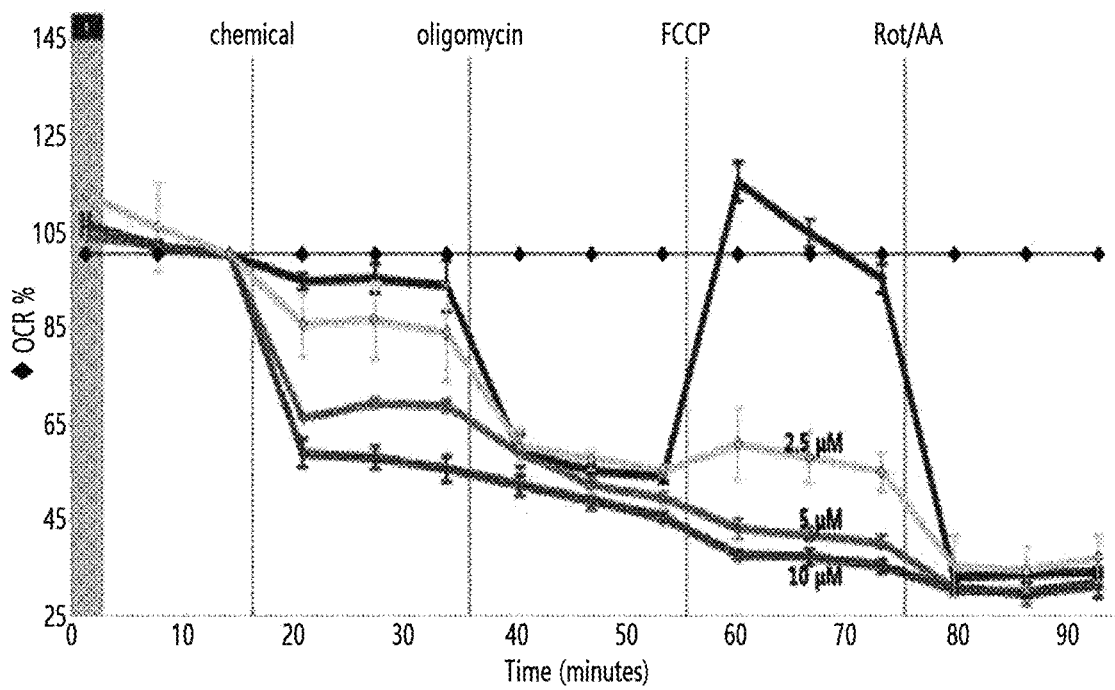
FIG. 2 shows the results of evaluating the mitochondrial inhibitory effects of compounds according to the present disclosure by measuring the changes in oxygen consumption rate (OCR) caused by treatment with the compounds.

The results are shown in FIG. 2.

As shown in FIG. 2, it was confirmed that treatment with the compounds according to the present disclosure reduced the mitochondrial oxygen consumption rate in a concentration-dependent manner, indicating that the compounds had a mitochondrial inhibitory effect.

In addition, the mitochondrial inhibitory effect in cancer cells by treatment with the compounds according to the present disclosure was evaluated by measuring hydrogen-ion gradient formation of mitochondrial transmembrane potential.

Specifically, mitochondrial transmembrane potential was analyzed by fluorescence-activated cell sorting (FACS) of cells stained with tetramethylrhodamine (TMRM, Invitrogen). Specifically, 300,000 MDA-MB-231 cells were seeded into a 60-mm dish, treated with each concentration of a drug for 16 hours, and then stained with 100 nM TMRM in HBSS for 30 minutes. After washing three times with HBSS, the cells were collected by trypsin treatment and analyzed by FACS.

Figure 3:
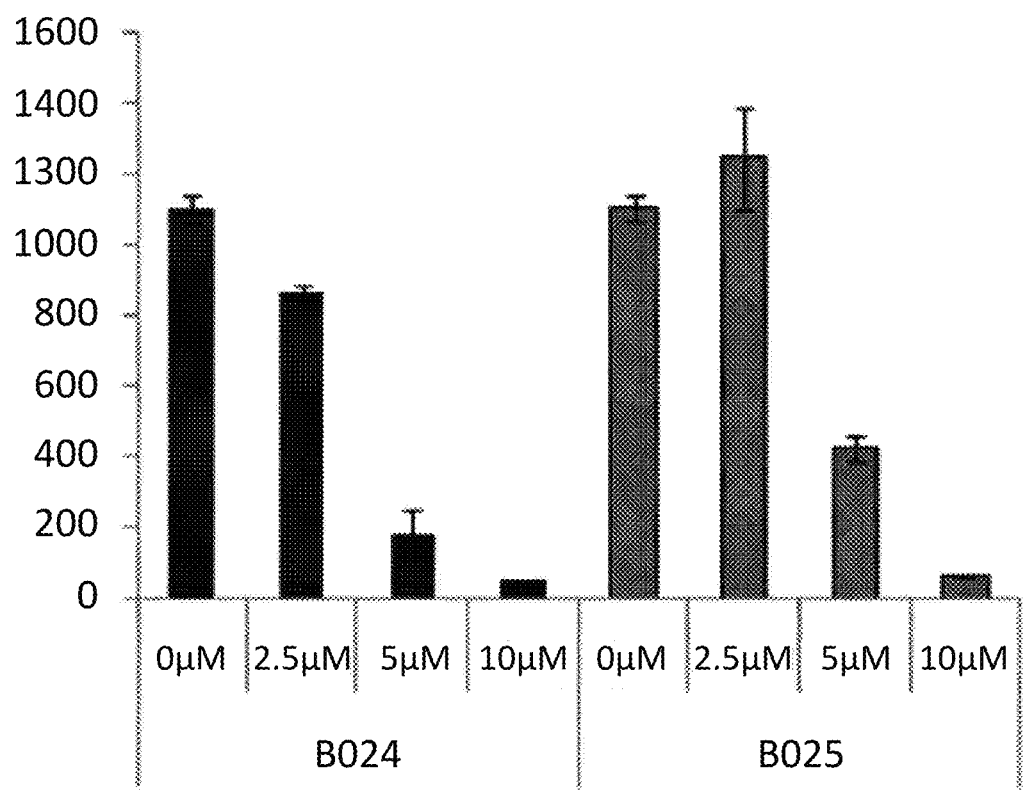
FIG. 3 shows the results of evaluating the mitochondrial inhibitory effects of compounds according to the present disclosure by measuring hydrogen-ion gradient formation of mitochondrial transmembrane potential using tetramethylrhodamine methyl ester (TMRM) after treatment with the compounds.

The results are shown in FIG. 3.

As shown in FIG. 3, it was confirmed that treatment with the compounds according to the present disclosure inhibited hydrogen-ion gradient formation of mitochondrial transmembrane potential in a concentration-dependent manner, indicating that the compounds according to the present disclosure exhibited a mitochondrial inhibitory effect in cancer cells.

Thereby, it was confirmed that the compounds according to the present disclosure induced cancer cell death by inhibiting mitochondria in cancer cells.

Example 7. Evaluation of Anticancer Effect in 3-Dimensional Tumor Spheroid Model The cancer growth inhibitory effect of administration of the compounds according to the present disclosure was evaluated using a 3D tumor spheroid model. The 3D tumor spheroid structure has characteristics similar to solid cancer under normal stress conditions because it is not easy to transfer nutrients into cancer cells.

Specifically, 7.5 K MDA-MB-321 cells were 3D-cultured in an ultra-low attachment (ULA) 96-well plate (Perkin Elmer) under a 2.5% Matrigel™ (BD Biosciences) condition. 5 days after 3D spheroid production, the cells were treated with various concentrations of the compound (#24) of Example 1 according to the present disclosure, and 14 days after the treatment, the cancer cell growth inhibitory effect of the compound was evaluated.

Figure 4:
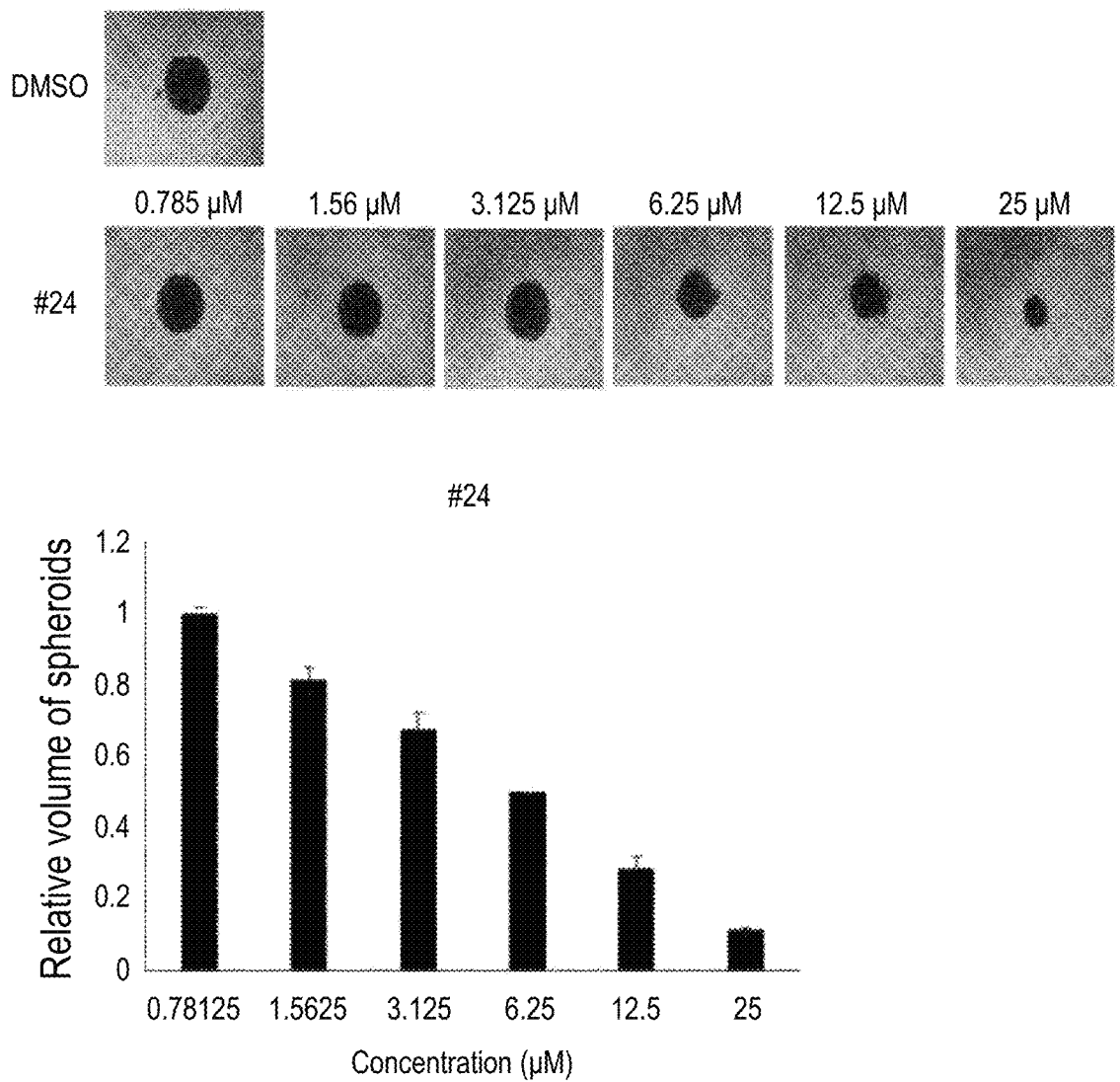
FIG. 4 shows the results of evaluating the anti-proliferative effect of compounds according to the present disclosure in a three-dimensional tumor spheroid model after treatment with the compounds.

The results are shown in FIG. 4.

As shown in FIG. 4, it was confirmed that treatment with the compound of Example 1 according to the present disclosure significantly inhibited cancer cell growth in the 3D tumor spheroid model in a concentration-dependent manner.

Example 8. Effect of Co-Administration with Paclitaxel on Promotion of Cancer Cell Death In order to evaluate the effect of co-treatment with paclitaxel (PTX) which is used as a chemotherapeutic agent against triple negative breast cancer, the effect of co-treatment was evaluated using a 3D tumor spheroid model in a manner similar to Example 7.

Specifically, 7.5 K MDA-MB-321 cells were 3D-cultured in an ultra-low attachment (ULA) 96-well plate (Perkin Elmer) under a 2.5% Matrigel™ (BD Biosciences) condition. 5 days after 3D spheroid production, the cells were co-treated with the compound (B024) of Example 1 according to the present disclosure and paclitaxel in a concentration-dependent manner, and 14 days after the treatment, the cancer cell growth inhibitory effect of co-treatment was evaluated.

Figure 5:
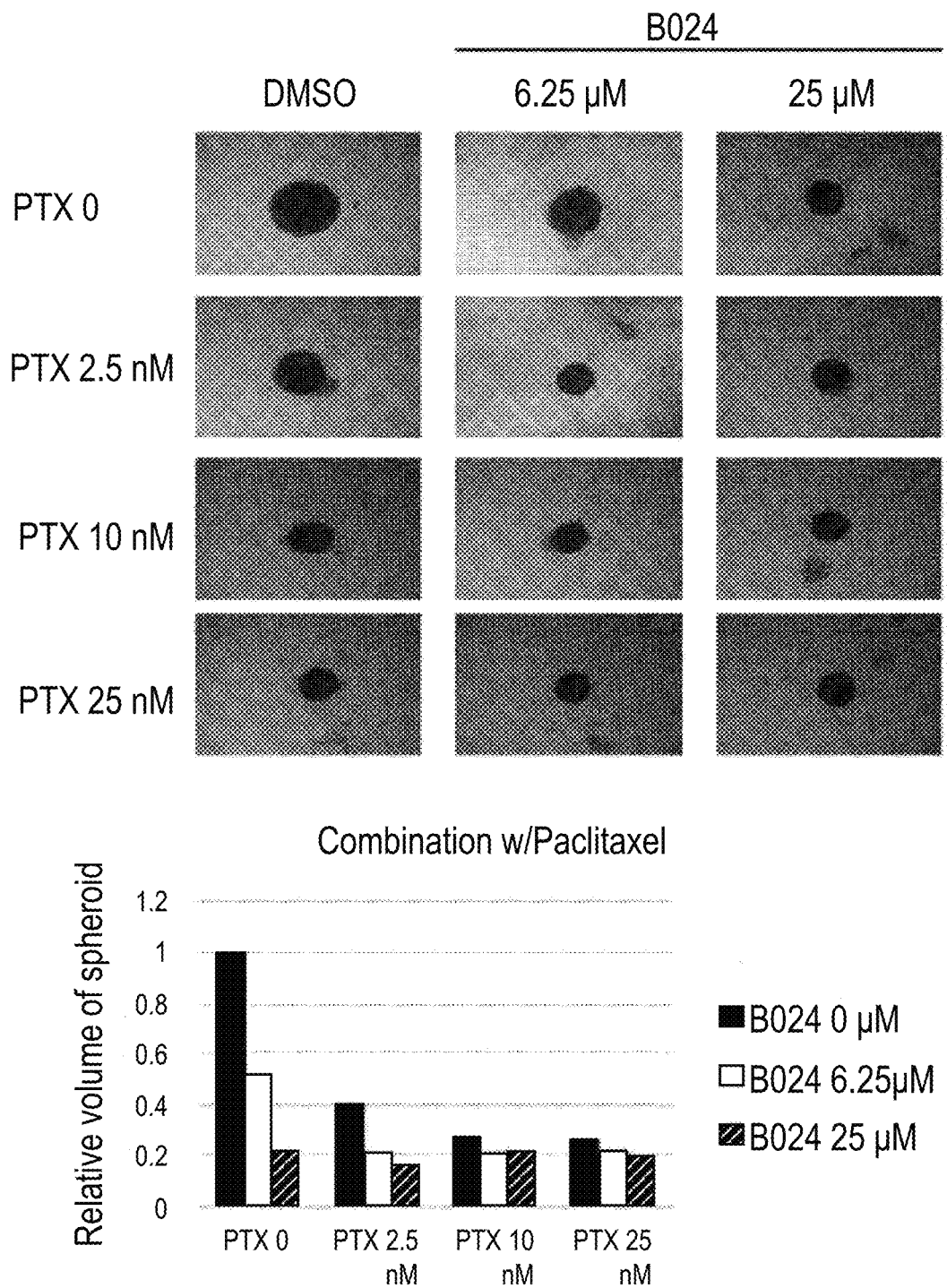
FIG. 5 shows the results of evaluating the anti-proliferative effect of combinations of a compound according to the present disclosure and paclitaxel in a three-dimensional tumor spheroid model after treatment with the combination.

The results are shown in FIG. 5.

As shown in FIG. 5, it was confirmed that co-administration of the compound (B024) of Example 1 and paclitaxel significantly inhibited cancer cell growth even at low concentrations.

Taking the above results together, it was confirmed that the novel biphenyl derivative compounds according to the present disclosure not only suppressed cancer metastasis and growth by increasing NDPK activity, but also significantly inhibited cancer growth by inhibiting the overall function of mitochondria under the glucose-deprived condition and inducing ATP depletion and cancer cell death. In addition, combinations of the compounds of the present disclosure with known anticancer agents not only exhibit excellent anticancer effects even at low concentrations, but also exhibit a maximized effect on cancer cell death through a synergistic effect. That is, the novel compounds according to the present disclosure exhibit an excellent effect of suppressing cancer metastasis and growth, and thus may be used as anticancer agents and anticancer adjuvants that exhibit excellent preventive and therapeutic effects.

Although the present disclosure has been described in detail with reference to the specific features, it will be apparent to those skilled in the art that this detailed description is only of a preferred embodiment thereof, and does not limit the scope of the present disclosure. Thus, the substantial scope of the present disclosure will be defined by the appended claims and equivalents thereto.

The invention claimed is:

1. A biphenyl derivative compound of Formula 1, an optical isomer thereof or a pharmaceutically acceptable salt thereof:

[Formula 1]

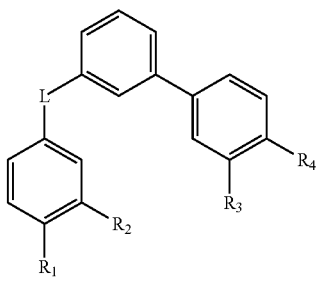

wherein

L is —(CH$_2$)—, —(C(=O))— or —(CHOH)—;

each of R$_1$, R$_2$, R$_3$ and R$_4$ is independently hydroxy or methoxy.

2. The biphenyl derivative compound, optical isomer thereof or pharmaceutically acceptable salt thereof according to claim 1, wherein each of R$_1$, R$_2$, R$_3$ and R$_4$ is methoxy.

3. The biphenyl derivative compound, optical isomer thereof or pharmaceutically acceptable salt thereof according to claim 1, wherein L is —(CH$_2$)— or —(CHOH)—.

4. The biphenyl derivative compound, optical isomer thereof or pharmaceutically acceptable salt thereof according to claim 1, wherein the compound of Formula 1 is selected from among the following compounds:

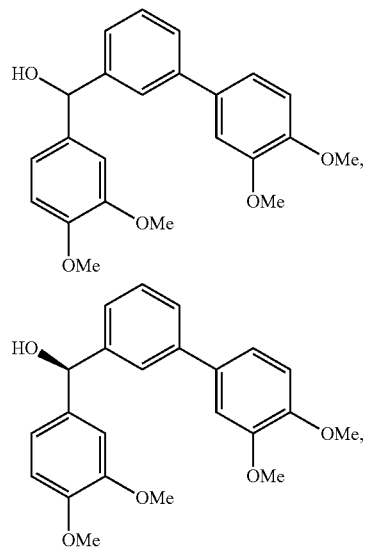

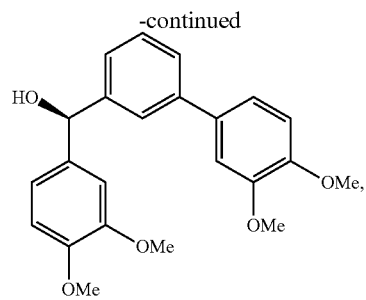

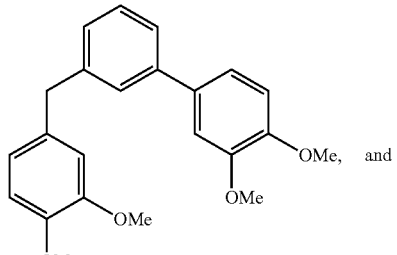

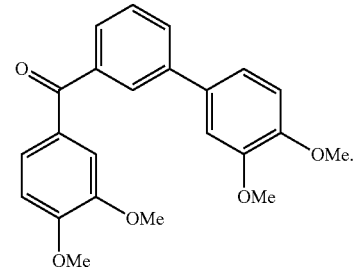

5. A pharmaceutical composition for treating cancer, the pharmaceutical composition containing, as an active ingredient, the biphenyl derivative compound, optical isomer thereof or pharmaceutically acceptable salt thereof according to claim 1, wherein the cancer is breast cancer.

6. The pharmaceutical composition of claim 5, further containing an anticancer agent that exhibits a synergistic effect with the biphenyl derivative compound, the optical isomer thereof or the pharmaceutically acceptable salt thereof.

7. The pharmaceutical composition of claim 6, wherein the anticancer agent is an anticancer agent selected from the group consisting of cisplatin, carboplatin, oxalliplatin, paclitaxel, docetaxel, vincristine, doxorubicin, daunorubicin, bleomycin, prednisone, methotrexate (MTX), 5-fluorouracil (5-FU), 6-mercaptopurine (6-MP), 6-thioguanine (6-TG), and combinations thereof.

8. A method for treating cancer, the method comprising a step of administering the pharmaceutical composition according to claim 5 to a subject that is or has developed cancer, wherein the cancer is breast cancer.

9. A composition for suppressing cancer metastasis, the composition containing, as an active ingredient, the biphenyl derivative compound, optical isomer thereof or pharmaceutically acceptable salt thereof according to claim 1, wherein the cancer is breast cancer.

10. A method for suppressing cancer metastasis, the method comprising a step of administering the composition according to claim 9 to a subject that is at risk of cancer metastasis or has metastasized cancer, wherein the cancer is breast cancer.

11. A food composition for alleviating cancer, the food composition containing, as an active ingredient, the biphenyl derivative compound, optical isomer thereof or pharmaceutically acceptable salt thereof according to claim 1, wherein the cancer is breast cancer.

12. The method of claim 8, further comprising a step of administering to the subject an anticancer agent selected from the group consisting of cisplatin, carboplatin, oxaliplatin, paclitaxel, docetaxel, vincristine, doxorubicin, daunorubicin, bleomycin, prednisone, methotrexate (MTX), 5-fluorouracil (5-FU), 6-mercaptopurine (6-MP), 6-thioguanine (6-TG), and combinations thereof.

* * * * *